US008563932B2

(12) United States Patent
Fang et al.

(10) Patent No.: US 8,563,932 B2
(45) Date of Patent: Oct. 22, 2013

(54) DEVICE AND METHOD FOR DIFFUSION OPTICAL TOMOGRAPHY

(75) Inventors: Wai-Chi Fang, Hsinchu (TW); Tien-Ho Chen, Hsinchu (TW); Shih Kang, Hsinchu (TW); Shih-Yang Wu, Hsinchu (TW); Ching-Ju Cheng, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 13/524,345

(22) Filed: Jun. 15, 2012

(65) Prior Publication Data

US 2013/0155388 A1 Jun. 20, 2013

(30) Foreign Application Priority Data

Dec. 14, 2011 (TW) .............................. 100146128 A

(51) Int. Cl.
*G01J 5/00* (2006.01)
(52) U.S. Cl.
USPC ...................................................... 250/338.1
(58) Field of Classification Search
USPC .......................................... 250/338.1–338.5
See application file for complete search history.

(56) References Cited

U.S. PATENT DOCUMENTS 8,314,406 B2 * 11/2012 Ntziachristos et al. .... 250/458.1
2011/0306857 A1 * 12/2011 Razansky et al. ............. 600/317

OTHER PUBLICATIONS

Zhang et al., "Experimental comparison of using continuous-wave and frequency-domain diffuse optical imaging systems to detect heterogeneities," 2001, SPIE Proceedings, vol. 4250, pp. 219-238.*
Kang et al., "Advanced Green Energy System-on-Chip Design for Portable Diffusion Optical Tomography", Department of Electronics Engineering and Institute of Electronics, National Chiao Tung University (Jun. 2011).

* cited by examiner

*Primary Examiner* — Kiho Kim
(74) *Attorney, Agent, or Firm* — Edwards Wildman Palmer LLP; Peter F. Corless; Steven M. Jensen

(57) ABSTRACT

A device and method for diffusion optical tomography are disclosed. The device includes a sensing circuit with a plurality of light sources and sensors and an optical tomography element having a control unit, a computation unit and an image reconstruction unit. First, the computation unit constructs an image model of an object using optical parameters of the object, and performs decomposition on the image model. Then, the control unit instructs the light sources to emit light to the object, and receives a plurality of optical signals generated by the object in response to the light. Finally, the image reconstruction unit combines the optical signals and the decomposed image model and reconstructs an image of the object based on the combination of the optical signals and the decomposed image model.

15 Claims, 4 Drawing Sheets

DEVICE AND METHOD FOR DIFFUSION OPTICAL TOMOGRAPHY

CROSS-REFERENCES TO RELATED APPLICATIONS

This application claims under 35 U.S.C. §119(a) the benefit of Taiwanese Application No. 100146128, filed Dec. 14, 2011, the entire contents of which is incorporated herein by reference.

FIELD OF THE INVENTION

The present invention relates to an image reconstruction technique for a target, and more particularly, to a device and method for performing image reconstruction on a target using diffusion optical tomography technology.

BACKGROUND OF THE INVENTION

In various current techniques for diagnosing chest or brain tumors, diffusion optical tomography (DOT) has become a popular method for its non-intrusive and real-time imaging features. Along with research developments and advances in manufacturing technologies, current diffusion optical tomography enables quick calculations on the results of image reconstruction, so diagnosis becomes safe and reliable.

Oxygenated and non-oxygenated hemoglobin have different levels of absorption to near-infrared light. Thus, diffusion optical tomography technology often uses near-infrared light in clinic trials related to blood flow, blood volume and oxygen saturation concentration, and also determine the presence of tumors based on the above biological signs.

However, as for the image reconstruction technique used after optical tomography, in order to meet the requirement for high image resolution, extremely large matrix operations often have to be performed on the tomography results. Huge matrix operations often results in long imaging time and a bulky system, and real-time scanning and real-time imaging cannot be realized. Thus, in current technologies, optical tomography and image reconstruction have to be performed in specific hospitals rather than in ordinary homes.

Thus, there is a need to solve the shortcomings such as no real-time imagining and large device size in the prior-art tomography technique.

SUMMARY OF THE INVENTION

In light of the foregoing drawbacks, the present invention provides a device and method for diffusion optical tomography.

The device for diffusion optical tomography according to the present invention includes a sensing circuit and an optical tomography element electrically connected to the sensing circuit. The sensing unit includes a plurality of light sources and a plurality of sensors. The plurality of light sources are used for emitting light to an object under test, so that the object generates a plurality of optical signals in response to the light, and the sensors are used for receiving the optical signals generated by the object. The optical tomography element is used for reconstructing an image of the object based on the optical signals outputted by the sensing circuit. The optical tomography element includes a control unit for controlling the sensing circuit to emit light to the object using the light sources and to receive the optical signals generated by the object in response to the light by the sensors; a computation unit for receiving optical parameters set for the object based on commands of the control unit, and constructing an image model of the object using the optical parameters of the object, so as to perform decomposition calculation on the image model for output; and an image reconstruction unit for receiving the optical signals of the object outputted by the control unit and the decomposed image model outputted by the computation unit based on commands of the control unit, and combining the decomposed image model and the optical signals to reconstruct the image of the object.

The above optical parameters of the object according to an embodiment of the present invention include one of more of a measured depth, adsorption coefficient, reflection coefficient or diffusion coefficient of the object.

The control unit according to an embodiment of the present invention is provided on a chip, and the sensing circuit is manufactured on a flexible printed circuit (FPC) electrically connected to the chip.

The method for diffusion optical tomography includes the steps below: (1) setting optical parameters of an object under test; (2) constructing an image model based on the optical parameters, performing decomposition on the image model to obtain a decomposed image model, and emitting light to the object by a plurality of light sources and sensing and receiving a plurality of optical signals generated by the object in response to the light; and (3) reconstructing an image of the object based on the optical signals and the decomposed image model.

The above step (2) further includes: (2-1) determining whether a predetermined number of optical signals have been received, if not, then continue sensing and receiving optical signals generated by the object until the number of the optical signals has reached the predetermined number; and (2-2) determining whether all the light sources have emitted light to the object, if not, then continue emitting light to the object until all of the light sources have emitted light to the object.

The device and method for diffusion optical tomography according to an embodiment of the present invention achieves image real-time processing and device miniaturization, which allows users to adhere the device onto any part of the body for performing optical tomography.

BRIEF DESCRIPTION OF THE DRAWINGS

The present invention can be more fully understood by reading the following detailed description of the preferred embodiments, with reference made to the accompanying drawings, wherein.

DETAILED DESCRIPTION OF THE EMBODIMENTS

The present invention is described by the following specific embodiments. Those with ordinary skills in the arts can readily understand the other advantages and functions of the present invention after reading the disclosure of this specification. The present invention can also be implemented with different embodiments. Various details described in this specification can be modified based on different viewpoints and applications without departing from the scope of the present invention.

Figure 1:
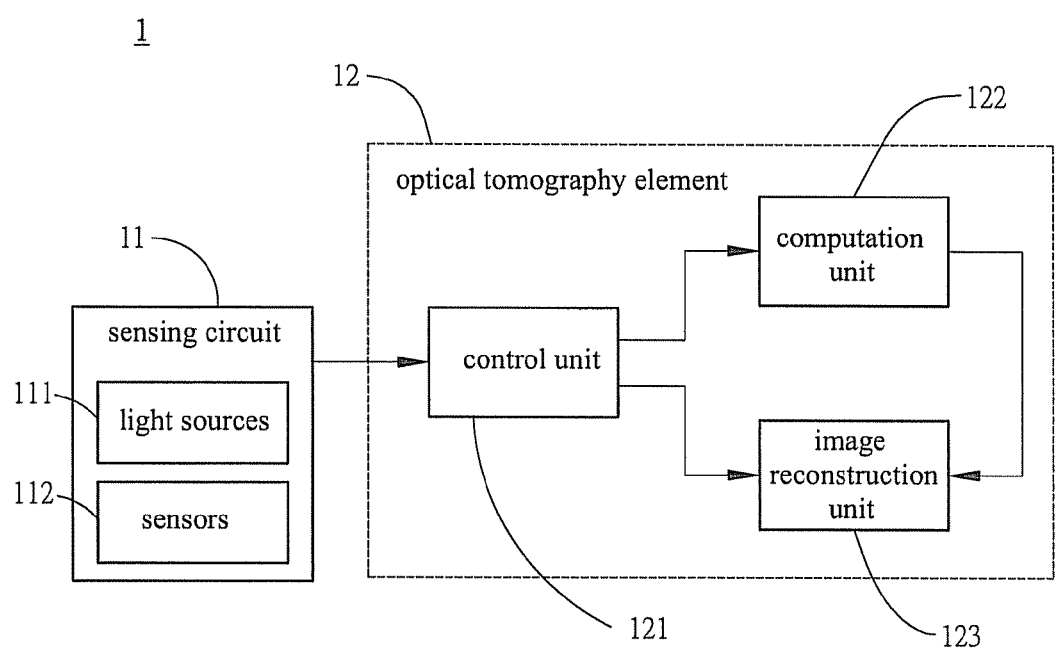
FIG. 1 is a block diagram illustrating a device for diffusion optical tomography according to an embodiment of the present invention.

Referring to FIG. 1, a block diagram illustrating a device for diffusion optical tomography according to the present invention is shown. As shown, the device for diffusion optical tomography 1 includes a sensing circuit 11 and an optical tomography element 12 connected with the sensing circuit 11.

The sensing circuit 11 includes a plurality of light sources 111 and a plurality of sensors 112. The plurality of light sources 111 each emits light to an object under test, such that the object generates a plurality of optical signals in response to the light (e.g. absorption, diffusion, scattering, refraction, reflection, etc.). The sensors 112 each receives optical signals generated by the object in response to the lights rays emitted by the light sources 111, and transmits them to a control unit 121.

The optical tomography element 12 is used for reconstructing an image of the object based on the plurality of optical signals outputted by the sensing circuit 11. The optical tomography element 12 includes the control unit 121, a computation unit 122 and an image reconstruction unit 123.

The control unit 121 is used for controlling the sensing circuit 11 to emit light to the object using each of the plurality of light sources 111 and to receive the optical signals generated by the object in response to the light by each of the sensors 112.

The computation unit 122 receives optical parameters set for the object based on commands of the control unit 121, constructs an image model of the object using the optical parameters of the object, performs decomposition calculation on the image model, and outputs the decomposed image model to the image reconstruction unit 123.

The image reconstruction unit 123 receives the optical signals outputted by the control unit 121 and the decomposed image model outputted by the computation unit 122 based on commands of the control unit 121, and combine the decomposed image model and the optical signals under the control of the control unit 121 in order to reconstruct the image of the object.

It should be noted that the optical parameters of the object may include the measured depth, adsorption coefficient, reflection coefficient or diffusion coefficient of the object, for example. The optical signals sensed by the of sensors 112 may represent biological information of the object in response to the light in terms of absorption, reflection, refraction, or the like. The light emitted by the light sources 111 may be continuous waves of near-infrared light with a wavelength of 735 nm or 890 nm. The light sources 111 do not have to emit light to the object all at the same time, but can emit light separately at different times based on control commands of the control unit 121.

The sensing circuit 11 can be manufactured onto a flexible printed circuit (FPC) in an actual implementation. The optical tomography element 12 can be a chip in an actual implementation, wherein the control unit 121, the computation unit 122 and image reconstruction unit 123 are manufactured on the chip, such that the chip is a system on chip (SOC).

Figure 2:
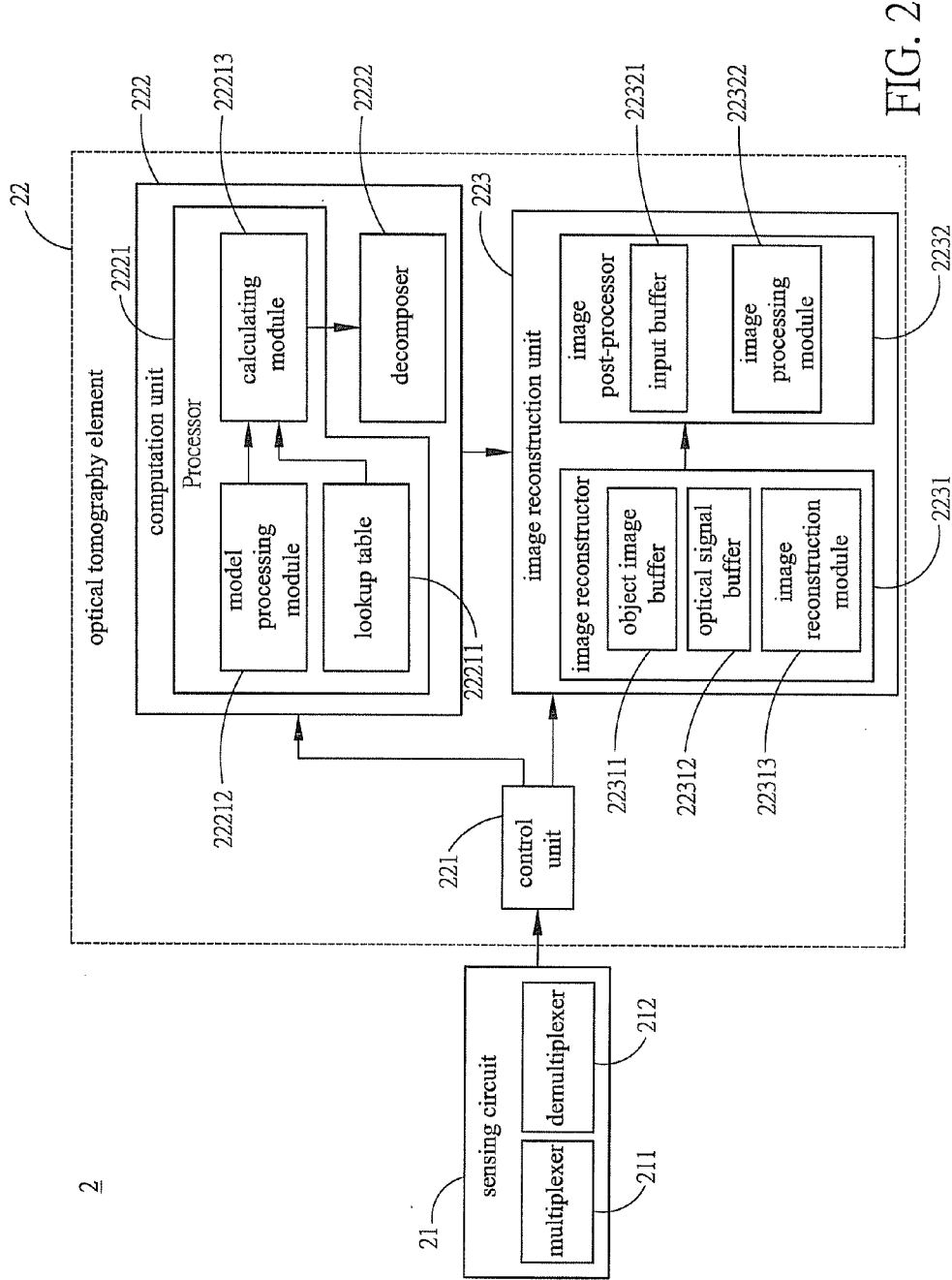
FIG. 2 is a block diagram illustrating a preferred embodiment of the device for diffusion optical tomography according to an embodiment of the present invention.

Referring to FIG. 2, a schematic diagram illustrating a preferred embodiment of the device for diffusion optical tomography according to the present invention is shown. As shown, a portable device for diffusion optical tomography 2 according to the embodiment of the present invention includes a sensing circuit 21 and an optical tomography element 22 connected with the sensing circuit 21. The sensing circuit 21 includes a multiplexer 211 and a demultiplexer 212. The optical tomography element 22 includes a control unit 221, a computation unit 222 and an image reconstruction unit 223.

The multiplexer 211 is used to enable specific one(s) of the light sources 111 so as to emit light to the object. The demultiplexer 212 is used to enable specific one(s) of the sensors 112 so as to receive the optical signals from the object.

In an implementation where the sensing circuit 21 is on a FPC, the light sources 111 and the plurality of sensors 112 (as shown in FIG. 1) can be provided on a side of the FPC facing the object. The multiplexer 211 and demultiplexer 212 (as shown in FIG. 2) are provided on a side of the FPC away from the object. A user may wear the FPC anywhere on the body with the side having the light sources and sensors thereon facing the body for sensing.

The computation unit 222 includes a processor 2221 and a decomposer 2222. The processor 2221 includes a lookup table 22211, a model processing module 22212, and a calculating module 22213.

The lookup table 22211 includes basic information of the sensing circuit 21, for example, the number of light sources, the predetermined number of sensors surrounding a light source, the relative distance between a light source and a sensor, the relative locations of the plurality of light sources with one another, the relative locations of the sensors with one another and the wavelength of the light emitted by the light sources, wherein the optical parameters can be set via an input interface (not shown) and input to the model processing module 22212.

The model processing module 22212 is used to receive the set optical parameters of the object and convert them into factors for matrix calculation.

The calculating module 22213 is used for performing calculation based on based on the factors generated by the model processing module 22212 and the basic information of the sensing circuit in the lookup table 22211 to construct a matrix of an image model of the object.

The decomposer 2222 performs decomposition on the matrix of the image model using singular value decomposition to obtain an inverse solution matrix, and then transmits the inverse solution matrix to the image reconstruction unit 223.

The image reconstruction unit 223 includes an image reconstructor 2231 and an image post-processor 2232.

The image reconstructor 2231 further includes an object image buffer 22311, an optical signal buffer 22312 and an image reconstruction module 22313. The optical signal buffer 22312 is used for buffering the plurality of optical signals. The object image buffer 22311 is used for buffering the inverse solution matrix. The image reconstruction module 22313 is used for processing each of the optical signals through a sub-frame algorithm to obtain sensing data of the object, and obtaining a scalar product of the sensing data and the inverse solution matrix to reconstruct the original image of the object.

The image post-processor 2232 further includes an input buffer 22321 and an image processing module 22322. The input buffer 22321 is used for buffering the original image. The image processing module 22322 performs weighted-array processing on the original image using the Gaussian function to obtain the final image of the object. The final image is then outputted via a display interface (not shown).

Since the plurality of optical signals received by the control unit 221 are responses coming from different regions of the object, so when the image reconstructor 2231 combines the optical signals and the image module of the object, the resulting image will have discontinuities at boundaries of neighboring regions. Thus, after the image reconstructor 2231 combines the plurality of optical signals and the image module and reconstructs the image of the object, the image postprocessor 2232 then performs smoothing process on the reconstructed image using the Gaussian algorithm, so the resulting image will have a better representation of the object.

Figure 3:
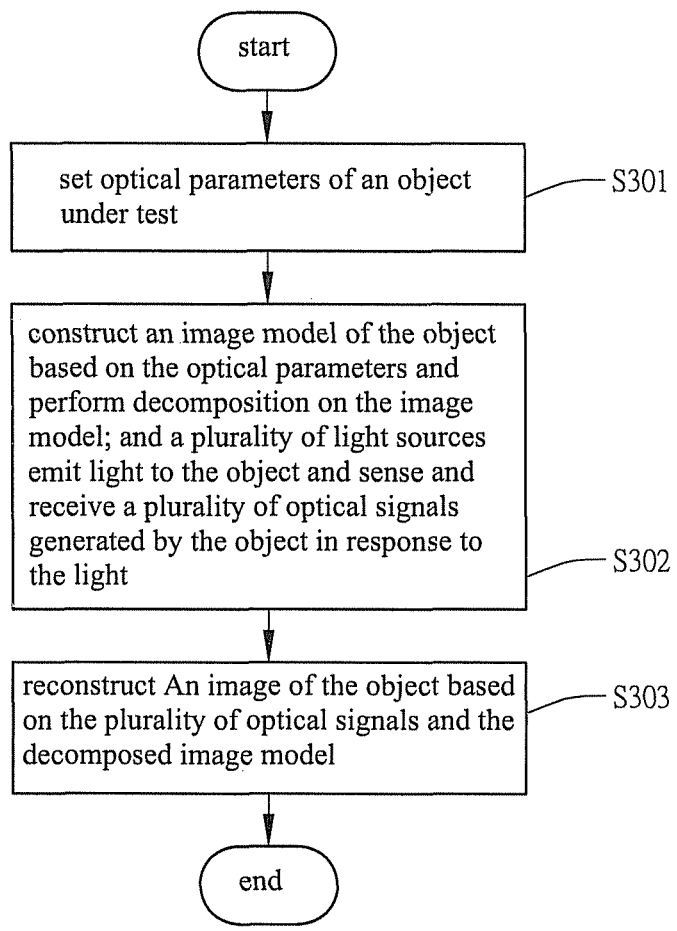
FIG. 3 is a flowchart illustrating a method for diffusion optical tomography according to an embodiment of the present invention.

Referring to FIG. 3, a flowchart depicting a method for diffusion optical tomography is shown. As shown, the method for diffusion optical tomography according to the present invention includes the following steps. In step S301, optical parameters of an object under test are set, then proceed to step S302. In step S302, an image model of the object is constructed based on the optical parameters and decomposition is performed on the image model to obtain a decomposed image model. Meanwhile, a plurality of light sources emit light to the object and a plurality of optical signals generated by the object in response to the light are sensed and received, then proceed to step S303, in which the image of the object is reconstructed based on the optical signals and the decomposed image model.

In the above step S302, it is further determined whether a predetermined number of optical signals have been received. If not, then continue sensing optical signals generated by the object until the number of received optical signals has reached the predetermined number. In addition, in step S302, singular value decomposition technique is used to perform decomposition on the image model to obtain the inverse solution matrix.

In step S303, the method further includes processing each of the optical signals through a sub-frame algorithm to obtain sensing data of the object, and obtaining a scalar product of the sensing data and the inverse solution matrix to reconstruct the original image of the object. After that, Gaussian extended algorithm is used to perform smoothing process on the image of the object.

Figure 4:
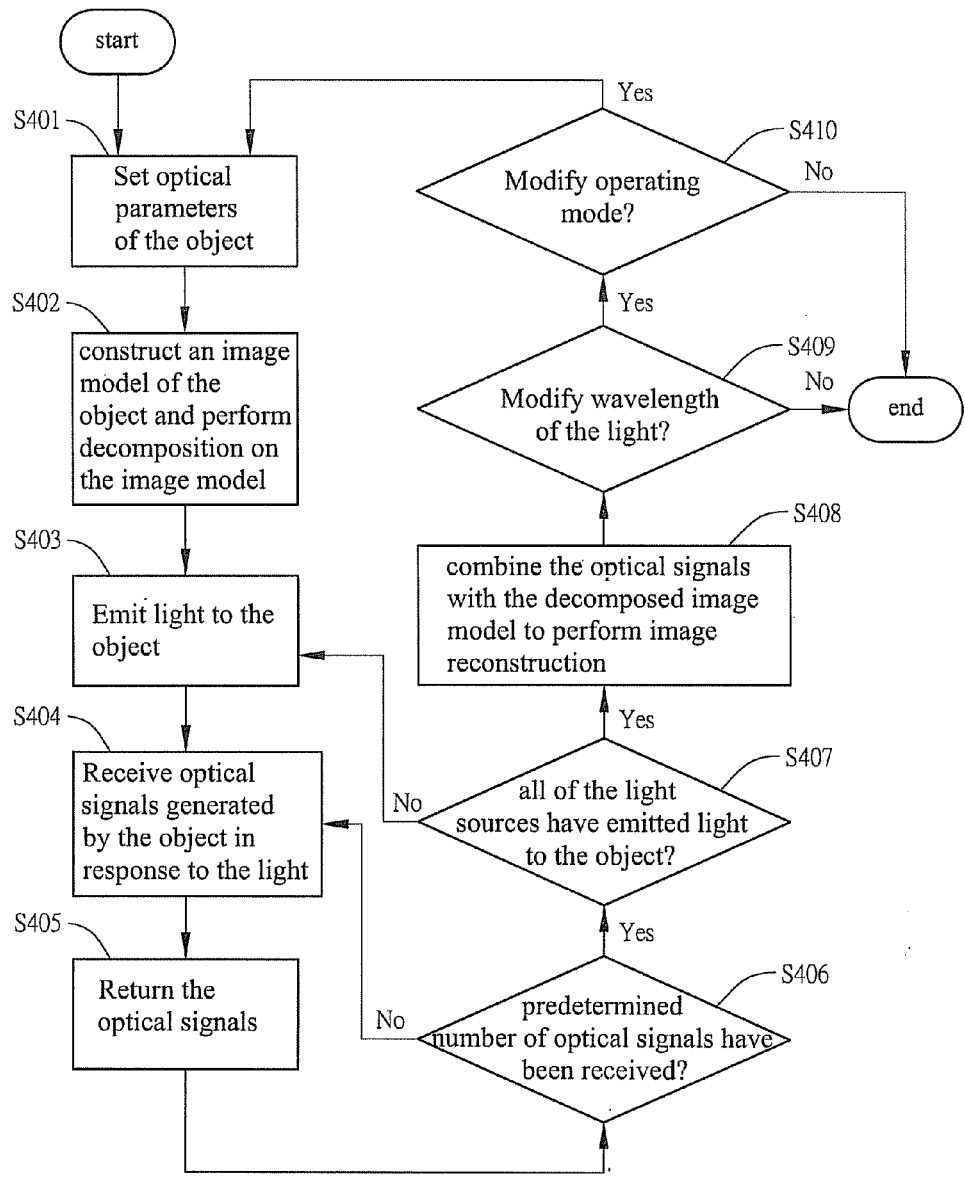
FIG. 4 is a flowchart illustrating a preferred embodiment of the method for diffusion optical tomography according to an embodiment of the present invention.

Referring to FIG. 4, a flowchart depicting a preferred embodiment of the method for diffusion optical tomography is shown. The method for diffusion optical tomography is applicable to the device for diffusion optical tomography, which at least includes a sensing circuit with a plurality of light source and sensors and an optical tomography element.

As shown, the method for diffusion optical tomography of this embodiment includes the following steps. First, in step S401, optical parameters such as measured depth, adsorption coefficient, reflection coefficient or diffusion coefficient of the object are set, then proceed to step S402. In step S402, an image model of the object is constructed based on the set optical parameters and decomposition is performed on the image model to obtain a decomposed image model. Then, proceed to step S403.

In step S403, light is emitted to the object, wherein the emitted light is continuous waves of near-infrared light. Then, proceed to step S404. In step S404, optical signals generated by the object in response to the light are received, then proceed to step S405, in which the optical signals are transmitted to the optical tomography element. Then, enter step S406.

In step S406, after the control unit has received the optical signals generated by the object in response to the light, it determines whether a predetermined number of optical signals have been received. If not, it means that the optical signals received are not complete, so return back to step S404 to receive more optical signals generated by the object in response to the light. If the determination result is positive, then proceed to step S407.

In this embodiment, each of the light sources emitting light is correspondingly surrounded by four sensors, for example. Thus, the predetermined number of optical signals described in step S406 is four. That is, in step S406, it is determined whether all four sensors have sensed and returned optical signals to the optical tomography element. However, the number of sensors surrounding the light source used herein is merely for illustration purpose and should not be construed in a limiting sense.

In step S407, it is determined if all of the light sources have emitted light to the object. If the determination result is negative, i.e. not all of the light sources on the sensing circuit have emitted light to the object, then return to steps S403 to emit light to the object. If the determination result is positive, then proceed to step S408 for image reconstruction.

In step S408, the optical signals are combined with the decomposed image model obtained in step S402 to perform image reconstruction, wherein a sub-frame algorithm is used to process each optical signal to obtain sensing data of the object, and the matrix of the image model is decomposed to obtain an inverse matrix solution, and then a scalar product of the sensing data and the inverse solution matrix is obtained to reconstruct the image of the object. Thereafter, Gaussian algorithm is performed on the reconstructed image for smoothing the discontinuities between boundaries therein, thereby enhancing the quality of the image. Then, proceed to step S409.

In step S409, it is determined if the wavelength of the light is to be modified. For example, the original wavelength is 735 nm, it is determined if the wavelength is to be modified to 890 nm. If not, the optical tomography process is ended; alternatively, return back to step S403 to start sensing again. If the wavelength of the light is to be modified, then proceed to step S410.

In step S410, it is determined if the operating mode is to be modified. If the operating mode is 1, it indicates no resetting of the optical parameters of the object is required. If the operating mode is 1, it indicates resetting of the optical parameters of the object is required. If the determination result is negative, then the optical tomography process is ended; alternatively, return to step S403 to start emitting light with the same wavelength to the object again. If the determination result is positive, then the optical parameters of the object are reset, and a light with a modified wavelength is used.

It should be noted that the order in which the constructing and decomposing of the image model described in step S402 and the emitting light to the object and receiving optical signals generated by the object in response to the light described in steps S403 to S406 are carried out are not limited to that described in the embodiment. In actual implementations, either the image model can be constructed first or the optical signals can be sensed first.

In summary, the device and method for diffusion optical tomography of the present invention minimizes traditional large machines used for diffusion optical tomography into a SoC chip and a FPC connected thereto. This allows users to adhere the device onto any part of the body. Compared to the other imaging systems that employ computers or other large equipment, the device and method of the present invention have the advantages of real-time imaging, low cost and high portability, making it more suitable for home care system.

Therefore, the present invention can be applied to the mammography, detection of hemorrhagic stroke, verification of cognitive functions in the brain and other related medical applications, allowing doctors to quickly grasp the condition of an illnesses or a combination with real-time monitoring in remote care system.

The above embodiments are only used to illustrate the principles of the present invention, and they should not be construed as to limit the present invention in any way. The above embodiments can be modified by those with ordinary skill in the art without departing from the scope of the present invention as defined in the following appended claims.

What is claimed is:

1. A device for diffusion optical tomography, comprising:
a sensing circuit having a plurality of light sources and a plurality of sensors, the light sources emitting light to an object, so that the object generates a plurality of optical signals in response to the light, and the sensors receive the optical signals generated by the object; and
an optical tomography element electrically connected to the sensing circuit for reconstructing an image of the object based on the optical signals outputted by the sensing circuit, the optical tomography element comprising:
a control unit for controlling the sensing circuit to emit light to the object using the light sources and to receive the optical signals generated by the object in response to the light by the sensors;
a computation unit for receiving optical parameters set for the object based on commands of the control unit, and constructing an image model of the object using the optical parameters of the object, so as to perform decomposition calculation on the image model for output; and
an image reconstruction unit for receiving the optical signals of the object outputted by the control unit and the decomposed image model outputted by the computation unit based on the commands of the control unit, and combining the decomposed image model and the optical signals to reconstruct the image of the object.

2. The device for diffusion optical tomography of claim 1, wherein the sensing circuit further comprises a multiplexer and a demultiplexer, the multiplexer is used to enable specific one or more of the light sources to emit light to the object, and the demultiplexer is used to enable specific one or more of the sensors to receive the optical signals from the object and transmit them to the control unit.

3. The device for diffusion optical tomography of claim 2, wherein the control unit is provided on a chip, and the sensing circuit is manufactured on a flexible printed circuit (FPC), and the plurality of light sources and sensors are provided on a side of the FPC facing the object, and the multiplexer and demultiplexer are provided on the other side of the FPC not away from the object.

4. The device for diffusion optical tomography of claim 1, wherein the optical parameters of the object comprise one or more of a measured depth, adsorption coefficient, reflection coefficient and diffusion coefficient.

5. The device for diffusion optical tomography of claim 1, wherein the optical signals generated by the object are biological information of different regions in the object.

6. The device for diffusion optical tomography of claim 1, wherein the computation unit comprises:
a processor comprising:
a model processing module for receiving the optical parameters of the object and converting them into factors for matrix calculation;
a lookup table including basic information of the sensing circuit; and
a calculating module for generating a matrix of the image model of the object based on the factors generated by the model processing module and the basic information of the sensing circuit stored in the lookup table; and
a decomposer for performing decomposition on the matrix of the image model using singular value decomposition to obtain an inverse solution matrix.

7. The device for diffusion optical tomography of claim 6, wherein the image reconstruction unit comprises:
an image reconstructor, comprising:
an object image buffer for buffering the optical signals;
an object image buffer for buffering the inverse solution matrix; and
an image reconstruction module for processing each optical signal through a sub-frame algorithm to obtain sensing data of the object, and obtaining a scalar product of the sensing data and the inverse solution matrix to reconstruct an original image of the object; and
an image post-processor including:
an input buffer for buffering the original image of the object; and
an image processing module for performing weighted-array processing on the original image using Gaussian function to obtain a final image of the object.

8. The device for diffusion optical tomography of claim 6, wherein the basic information of the sensing circuit is at least one selected from the group consisting of the number of the light sources and their relative locations to one another, the number of the sensors and their relative locations to one another, the distance between each of the light sources and each of the sensors and the wavelength of the light emitted by the light sources.

9. The device for diffusion optical tomography of claim 1, wherein the light emitted by the light sources is continuous waves of near-infrared light.

10. A method for diffusion optical tomography, comprising the steps below:
(1) setting optical parameters of an object;
(2) constructing an image model based on the optical parameters, performing decomposition on the image model to obtain a decomposed image model, and emitting light to the object by a plurality of light sources and sensing and receiving a plurality of optical signals generated by the object in response to the light; and
(3) reconstructing an image of the object based on the optical signals and the decomposed image model.

11. The method for diffusion optical tomography of claim 10, wherein step (2) further comprises:
(2-1) determining whether a predetermined number of optical signals have been received, if not, then continue sensing and receiving optical signals generated by the object until the number of the optical signals has reached the predetermined number; and
(2-2) determining whether all the light sources have emitted light to the object, if not, then continue emitting light to the object until all of the light sources have emitted light to the object.

12. The method for diffusion optical tomography of claim 10, further comprising (4) modifying wavelength of the light and then returning to steps (1) to (3) again.

13. The method for diffusion optical tomography of claim 10, wherein, in step (2), decomposition on the image model includes using singular value decomposition to decompose an matrix of the image model to obtain an inverse solution matrix.

14. The method for diffusion optical tomography of claim 13, wherein step (3) further comprises:
- (3-1) processing each optical signal through a sub-frame algorithm to obtain sensing data of the object, and obtaining a scalar product of the sensing data and the inverse solution matrix to reconstruct the image of the object; and
- (3-2) performing a smoothing process on the reconstructed image of the object using Gaussian function.

15. The method for diffusion optical tomography of claim 10, wherein the light emitted by the light sources is continuous waves of near-infrared light.

\* \* \* \* \*